United States Patent [19]
Green et al.

[11] Patent Number: 5,417,698
[45] Date of Patent: May 23, 1995

[54] APPARATUS FOR TIGHTENING ELONGATED WOUND CLOSURE ELEMENTS

[75] Inventors: David T. Green, Westport; Henry Bolanos, East Norwalk; Thomas W. Alesi, Jr., New Fairfield, all of Conn.; Kenneth E. Toso, Portchester, N.Y.

[73] Assignee: United States Surgical Corporation, Norwalk, Conn.

[21] Appl. No.: 959,212

[22] Filed: Oct. 9, 1992

[51] Int. Cl.$^6$ ............................................. B25B 25/00
[52] U.S. Cl. .................................... 606/139; 140/123.5
[58] Field of Search ................. 606/139, 151, 213; 24/16 PB; 140/93.2, 123.5, 123.6

[56] References Cited

U.S. PATENT DOCUMENTS

| | | |
|---|---|---|
| 1,717,766 | 6/1929 | Eimler . |
| 1,950,799 | 3/1934 | Jones . |
| 2,622,292 | 12/1952 | Pehaczek . |
| 2,650,510 | 9/1953 | Hart . |
| 2,948,939 | 8/1960 | Prete, Jr. . |
| 2,987,062 | 6/1961 | Ellison . |
| 3,111,945 | 11/1963 | Von Solbrig . |
| 3,118,473 | 1/1964 | Bell ............................ 24/16 PB |
| 3,469,573 | 9/1969 | Florio . |
| 3,473,528 | 10/1969 | Mishkin et al. . |
| 3,570,497 | 3/1971 | Lemole . |
| 3,577,601 | 5/1971 | Mariani . |
| 3,802,438 | 4/1974 | Wolvek . |
| 3,931,838 | 1/1976 | Bakermans . |
| 4,037,603 | 7/1977 | Wendorff . |
| 4,119,091 | 10/1978 | Partridge . |
| 4,136,422 | 1/1979 | Ivanov et al. . |
| 4,201,215 | 5/1980 | Crossett et al. . |
| 4,202,384 | 5/1980 | Aubert . |
| 4,252,158 | 2/1981 | McDade . |
| 4,263,904 | 4/1981 | Judet . |
| 4,279,248 | 7/1981 | Gabbay . |
| 4,387,489 | 6/1983 | Dudek . |
| 4,390,047 | 6/1983 | Kaneko . |
| 4,512,346 | 4/1985 | Lemole . |
| 4,535,764 | 8/1985 | Ebert . |
| 4,542,883 | 9/1985 | Rutzki . |
| 4,561,475 | 12/1985 | Hinden . |
| 4,574,848 | 3/1986 | Bartzick et al. . |
| 4,583,541 | 4/1986 | Barry . |
| 4,625,717 | 12/1986 | Covitz . |
| 4,643,178 | 2/1987 | Nastari et al. . |
| 4,667,662 | 5/1987 | Titone et al. . |
| 4,730,615 | 3/1988 | Sutherland et al. . |
| 4,754,530 | 7/1988 | Lindblad . |
| 4,792,336 | 12/1988 | Hlavacek et al. . |
| 4,802,477 | 2/1989 | Gabbay . |
| 4,804,383 | 2/1989 | Rey et al. . |
| 4,813,416 | 3/1989 | Pollak et al. . |
| 4,878,271 | 11/1989 | Kitokovsky ............................ 24/194 |
| 4,896,668 | 1/1990 | Popoff et al. ............................ 606/74 |
| 4,920,959 | 5/1990 | Witzel et al. ............................ 606/53 |
| 4,943,292 | 7/1990 | Foux ............................ 606/70 |
| 4,944,753 | 7/1990 | Burgess et al. ............................ 623/16 |
| 4,947,901 | 8/1990 | Rancour et al. ............................ 140/93.2 |
| 4,955,913 | 9/1990 | Robinson ............................ 606/228 |
| 4,966,600 | 10/1990 | Songer et al. ............................ 606/74 |
| 5,024,618 | 6/1991 | Tepic ............................ 606/53 |
| 5,029,433 | 7/1991 | Werk ............................ 53/592 |
| 5,048,575 | 9/1991 | Smith ............................ 140/93.2 |
| 5,058,365 | 10/1991 | Kägi ............................ 53/582 |
| 5,089,012 | 2/1992 | Prou ............................ 606/224 |
| 5,139,498 | 8/1992 | Ley ............................ 606/69 |
| 5,163,598 | 11/1992 | Peters et al. ............................ 227/176 |

FOREIGN PATENT DOCUMENTS

| | | |
|---|---|---|
| 0117981 | 9/1984 | European Pat. Off. . |
| 0371290 | 6/1990 | European Pat. Off. . |
| 1130000 | 1/1957 | France . |
| 9210460 | 8/1992 | France . |
| 2730571 | 1/1978 | Germany . |
| 3042699 | 6/1981 | Germany . |
| 3244680 | 6/1984 | Germany . |
| 303821 | 2/1955 | Switzerland . |
| WO91/04137 | 4/1991 | WIPO . |

*Primary Examiner*—Tamara L. Graysay

[57] ABSTRACT

An instrument for tightening wound closure elements around body tissue, such as a human sternum following surgery. The instrument includes a first handle and a second handle pivotally attached to the first handle and movable between an open and a closed position. A retaining system is also provided to tighten wound closure material in response to movement of the second handle.

20 Claims, 12 Drawing Sheets

APPARATUS FOR TIGHTENING ELONGATED WOUND CLOSURE ELEMENTS

BACKGROUND OF THE INVENTION

1. Field of the Invention

This invention relates to an instrument for tightening elongated wound closure elements around body tissue and, in particular, for tightening wound closure elements around the human sternum following surgery.

2. Background of the Related Art

Sternum repair may be required as a result of either cardiac surgery or direct injury to the sternum. In order to perform various cardiac surgical procedures, the sternum must first be halved to permit access to the heart, and then rejoined upon completion of the primary surgical procedure. The need for ensuring tight and secure closure of a wound closure element in any situation cannot be overstated, particularly when the closure element is designed for closing the human sternum. Insufficient sternum closure following surgery not only prohibits osteosynthesis, but also can cause dangerous sternum infection.

Presently, there are many known products for repairing the sternum and/or human body tissue in areas where a repair may be required either as a result of injury or a surgical procedure. Such wound closure products can include wires, sutures, ribbons or widened and elongated straps which are wrapped around the body part to be repaired. These wound closure products can be manufactured from a variety of materials including surgical gut, silk, cotton, or a polyolefin such as polypropylene, polyamide, polyglycolic acids, and polyesters such as polyethylene, terepthalate and glycolide-lactide copolymer.

One particular device for sternum closure is the Controlled Tension Osteosynthesis System which was developed by Dr. Josef Vincent and is described in *The Annals of Thoracic Surgery*, Volume 41, Number 2 (February 1986). This system discloses a stainless steel plate which is mounted across the halved sternum and is anchored by a series of wires placed through or around the sternum. Also disclosed in this system is a device for straining the wire mounted through the anchor plate to the desired tension, where the device then trims the wire to the correct size. While this is a useful system for closing the sternum, there are several disadvantages to using this procedure. One drawback of this procedure is that the wires are difficult to position while another more dangerous drawback is that the wires can injure arteries during their placement in the bone. Another major disadvantage of using wires is that a wire can slice through thin or osteoporotic bone thereby destroying the compression rigidity of the sternal closure.

In order to overcome the drawbacks of the wire sternum closure, elongated straps or ribbons are often utilized. In sternum closure devices which utilize elongated straps or ribbons, such as is disclosed in U.S. Pat. No. 4,813,416 and U.S. Pat. No. 4,201,215, tightening and adjusting the straps is often difficult to perform and requires the use of two hands, one to hold one end of the ribbon stationary and a second hand to adjust, tighten and trim the opposite ribbon end.

SUMMARY OF THE INVENTION

The present invention overcomes the problems and deficiencies of the prior art by providing an apparatus for tightening an elongated wound closure material about tissue. The apparatus comprises frame means, handle means pivotally mounted about a pivot pin to the frame means, a wound closure material adapted to be looped about tissue and retaining means positioned adjacent the handle means for retaining one end portion of the would closure material in a generally fixed position relative to the handle means whereby pivotal movement of the handle means in a first direction advances the wound closure material in a tensioning direction about the tissue.

In a preferred embodiment, the apparatus for tightening an elongated wound closure material about tissue comprises frame means, handle means pivotally mounted about a pivot pin to the frame means and a pincher assembly pivotally mounted to the frame means about the pivot pin and pivotally movable relative to the handle means between an open and a closed position. The pincher assembly securely wedges one end portion of the wound closure element against a bearing surface defined by the handle means when in the closed position and permits passage of the one end portion of the wound closure element between the pincher assembly and the bearing surface when in the open position. The preferred pincher assembly comprises at least one linkage member pivotally mounted at a first end portion thereof to the pivot pin and an engaging member mounted to the linkage member at a second end portion thereof. The engaging member engages the one end portion of the wound closure element when the pincher assembly is in the closed position.

In an alternative preferred embodiment, the apparatus comprises a wound closure material adapted to be looped about split portions of tissue and having first and second end portions with a locking device attached to the first end portion thereof, frame means defining an opening formed in a lower surface thereof whereby the opening is dimensioned and configured to receive and support the locking device, handle means pivotally mounted about a pivot pin to the frame means and retaining means positioned adjacent the handle means for retaining the second end portion of the wound closure material in a generally fixed position relative to the handle means. Pivotal movement of the handle means in a first direction advances the wound closure material in a tensioning direction about the tissue.

BRIEF DESCRIPTION OF THE DRAWINGS

The present invention will be more fully appreciated as the same becomes better understood from the following detailed description of the present invention when considered in connection with the accompanying drawings in which.

DETAILED DESCRIPTION OF THE PREFERRED EMBODIMENTS

Figure 1:
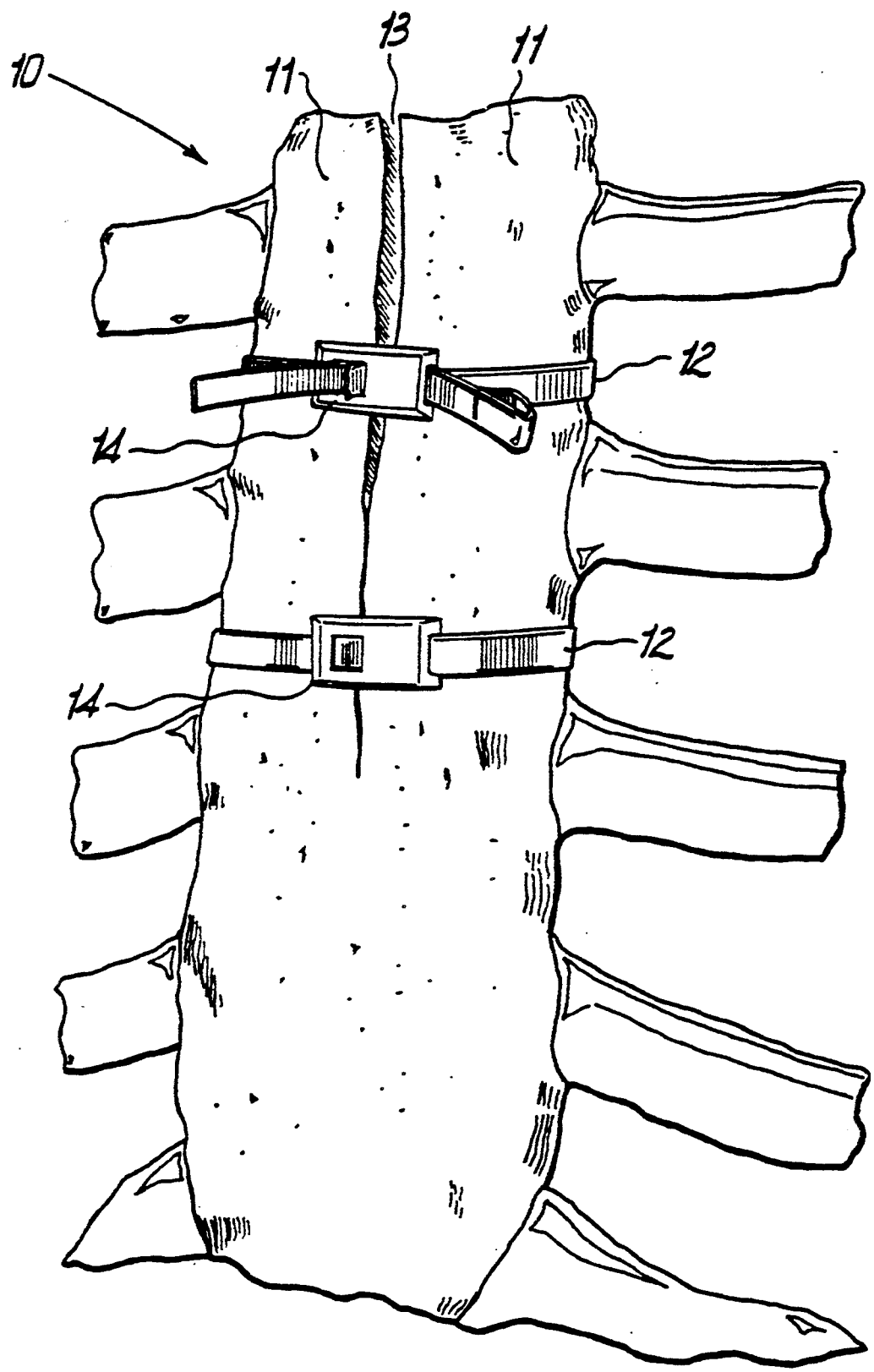
FIG. 1 illustrates a surgical wound closure element wrapped around the human sternum.
Figure 2:
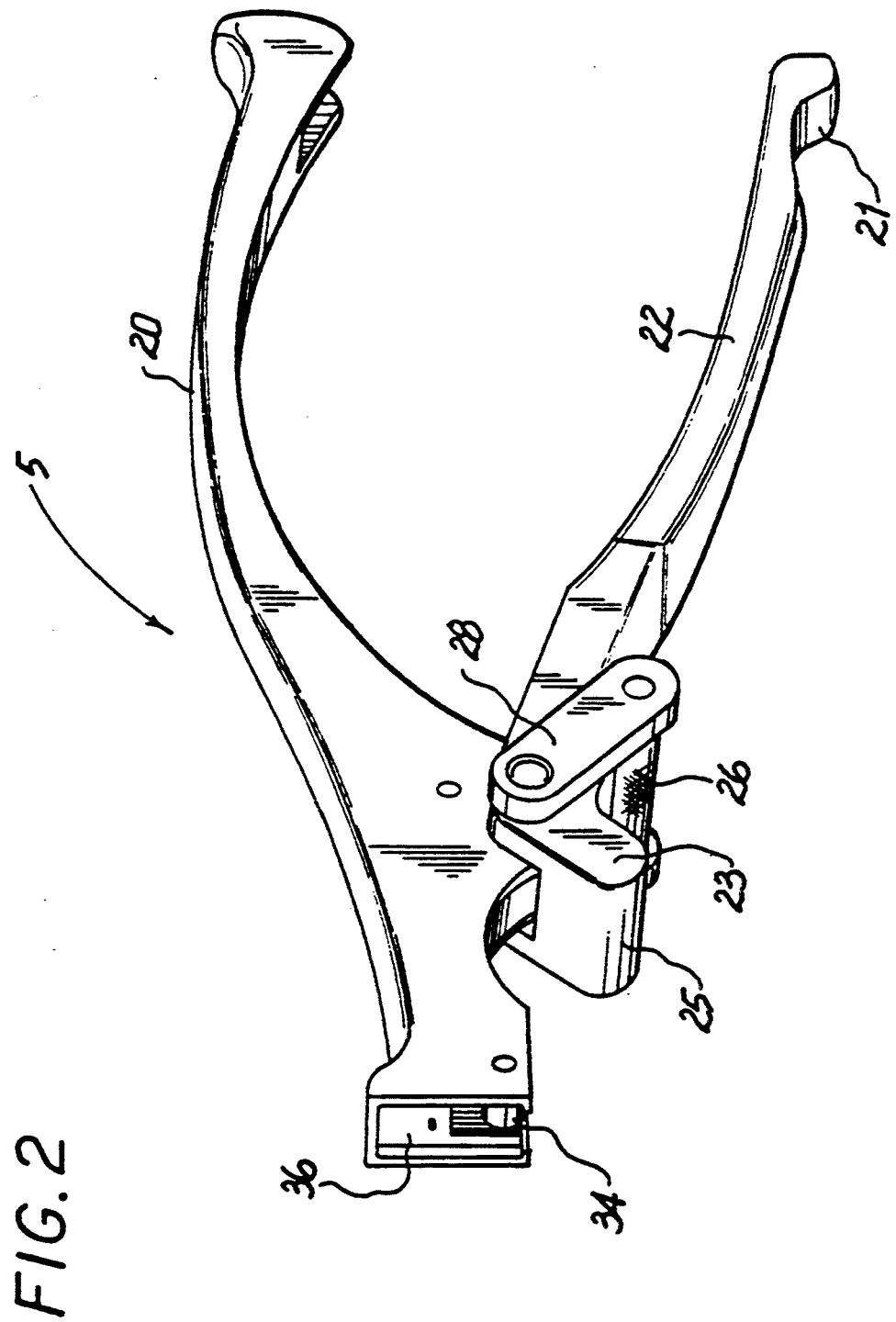
FIG. 2 is a perspective view of one embodiment of an instrument of the present invention for tightening the wound closure element around the sternum.

Referring to FIG. 1, a wound closure element is shown looped about a human sternum 10. The wound closure element comprises a ribbon or strap 12 which is inserted through and retained by a tightening plate or buckle 14. Buckle 14 rests against the sternum 10, preferably transversely centered along opening 13 formed between split portions 11 of the sternum, to secure ribbon 12 against the sternum 10. When sufficient tensioning force is applied to the wound closure element 12, typically by pulling one of its ends, the split portions 11 of sternum 10 are moved into abutment to close opening 13. The tensioning force is significant since inadequate tensioning will not satisfactorily hold the sternum halves in abutment and will inhibit proper healing and possibly cause an infection. On the other hand, excessive tensioning could result in the ribbon breaking.

The present invention provides several instruments which are utilized to tighten elongated wound closure elements around body tissue. For purposes of discussion below, the instrument will be described for use with the wound closure element depicted in FIG. 1 for closing a sternum incision. However, it should be noted that the instruments of the present invention can be utilized with other wound closure elements and can be used to seal openings or incisions in other body parts.

In each of the embodiments of the instrument which is the subject of the present invention, the ribbon 12 of the wound closure element is routed through the instrument, a housing portion is placed over the buckle 14, and the handle is moved to its closed position to pull the ribbon 12 tighter around the sternum. In the embodiments of FIGS. 2-5 and 6-7, the ribbon is manually pulled by the user's hand after each pivotal movement of the handle to remove the slack created by tightening the ribbon. In the embodiment of FIGS. 8-11, pivotal movement of the handle actuates a driver to continuously pull the strap without manual manipulation. Each of these embodiments is discussed below in detail.

Referring now to FIGS. 2-5, one embodiment of the instrument of the present invention is illustrated. The instrument, designated generally by reference numeral 5, includes frame 20 and handle 22 pivotably mounted thereto for movement between an open position spaced from frame 20 and a closed position towards frame 20. Handle 22 is illustratively L-shaped in configuration with a proximal end portion 21 adapted to be gripped by the user and a leg portion 23 at its distal end having an outer abutment surface 25, shown in FIG. 5, adapted to contact one side of ribbon 12 when routed through the instrument.

Figure 5:
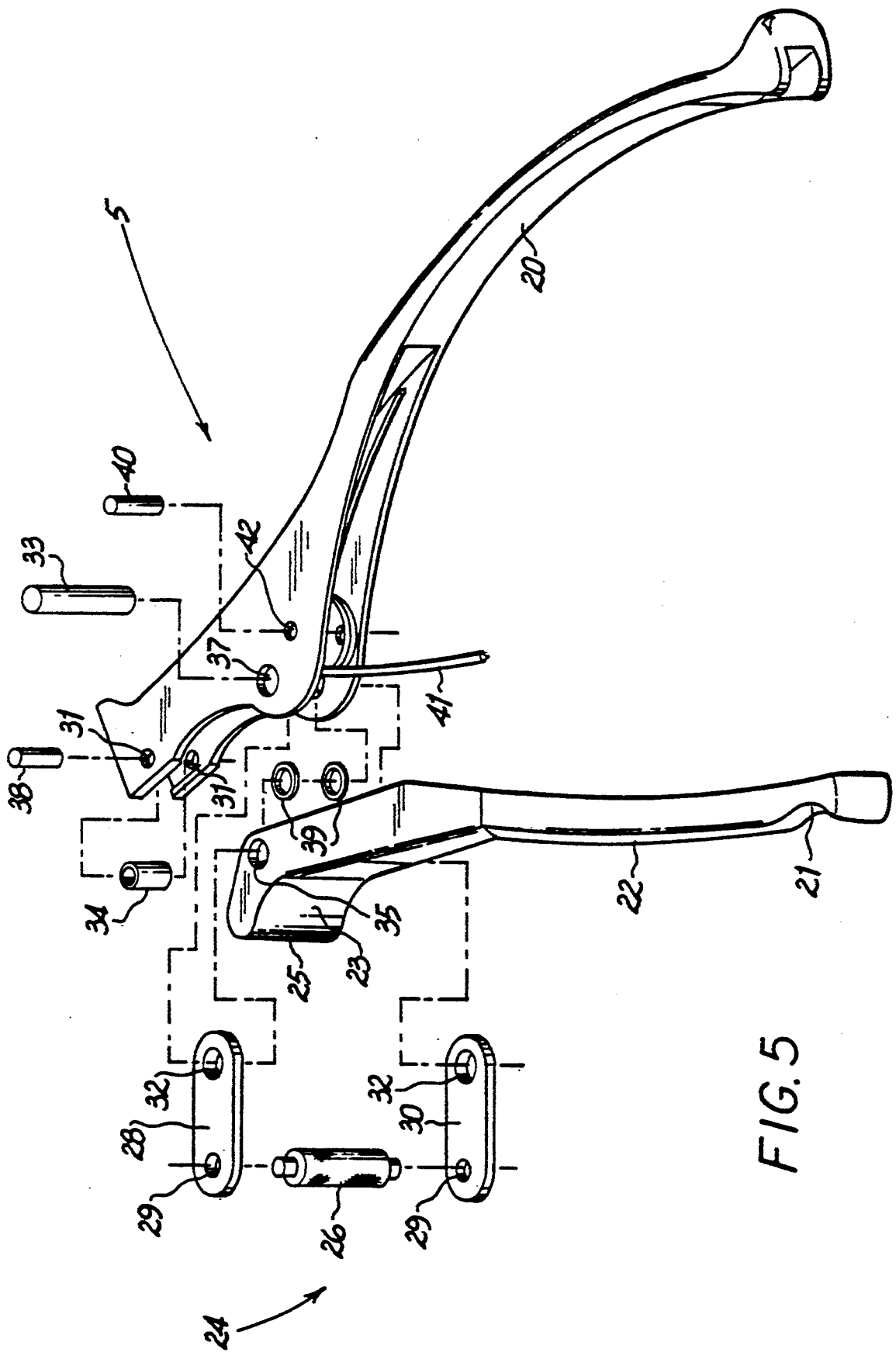
FIG. 5 is an exploded view showing the components of the instrument of FIG. 1.

Referring to FIG. 5, mounted to leg portion 23 is pincher assembly 24 which includes left ear or left linkage member 28, right ear or right linkage member 30 and roller or engaging member 26 securely positioned therebetween. Both left and right ears 28 and 30 each have an aperture 29 formed in their outer ends which is dimensioned to receive the reduced diameter ends of roller 26. As will become apparent from the discussion below, roller 26 is adapted to come into contact with the side of ribbon 12 which is opposite the side that contacts bearing or abutment surface 25. Roller 26 is preferably knurled to reduce slippage of the ribbon 12.

An opening 32 is formed at the inner end of both left and right ears 28 and 30 for alignment with openings 35 in frame portion 22 and openings 37 in handle 20. Mounting pin 33 extends through aligned openings 32, 35 and 37, thereby functioning not only to pivotably mount handle 22 to frame 20, but to pivotally mount ears 28 and 30 to handle 22. Washers 39 are positioned on opposing sides of mounting pin 33 between the portion of frame 20 and the portion of handle 22 which form the pivotal connection between the frame and the handle. For reasons which will be explained below, ears 28 and 30 are mounted to handle 22 for pivotal movement between a lower position wherein roller 26 is adjacent abutment surface 25 of handle 22 and an upper position wherein roller 26 is spaced away from abutment surface 25.

Referring once again to FIGS. 2-5, a support member in the form of bottom recess 36 of frame 20 is configured and dimensioned to receive buckle 14 and a portion of ribbon 12. Roller 34, illustratively hollow, is mounted to a bottom portion of frame 20 (see also FIG. 3) adjacent to recess 36, by transverse pin 38 extending through opposing apertures 31. Roller 34 is provided to retain ribbon 12 in position within frame 20 and to facilitate movement of the ribbon when pulled during the tightening procedure.

Rod 40 extends through openings 42 in frame 20 to retain spring 41 within frame 20. Spring 41 is provided to normally bias handle 22 away from frame 20, as shown in FIG. 1.

Figure 3:
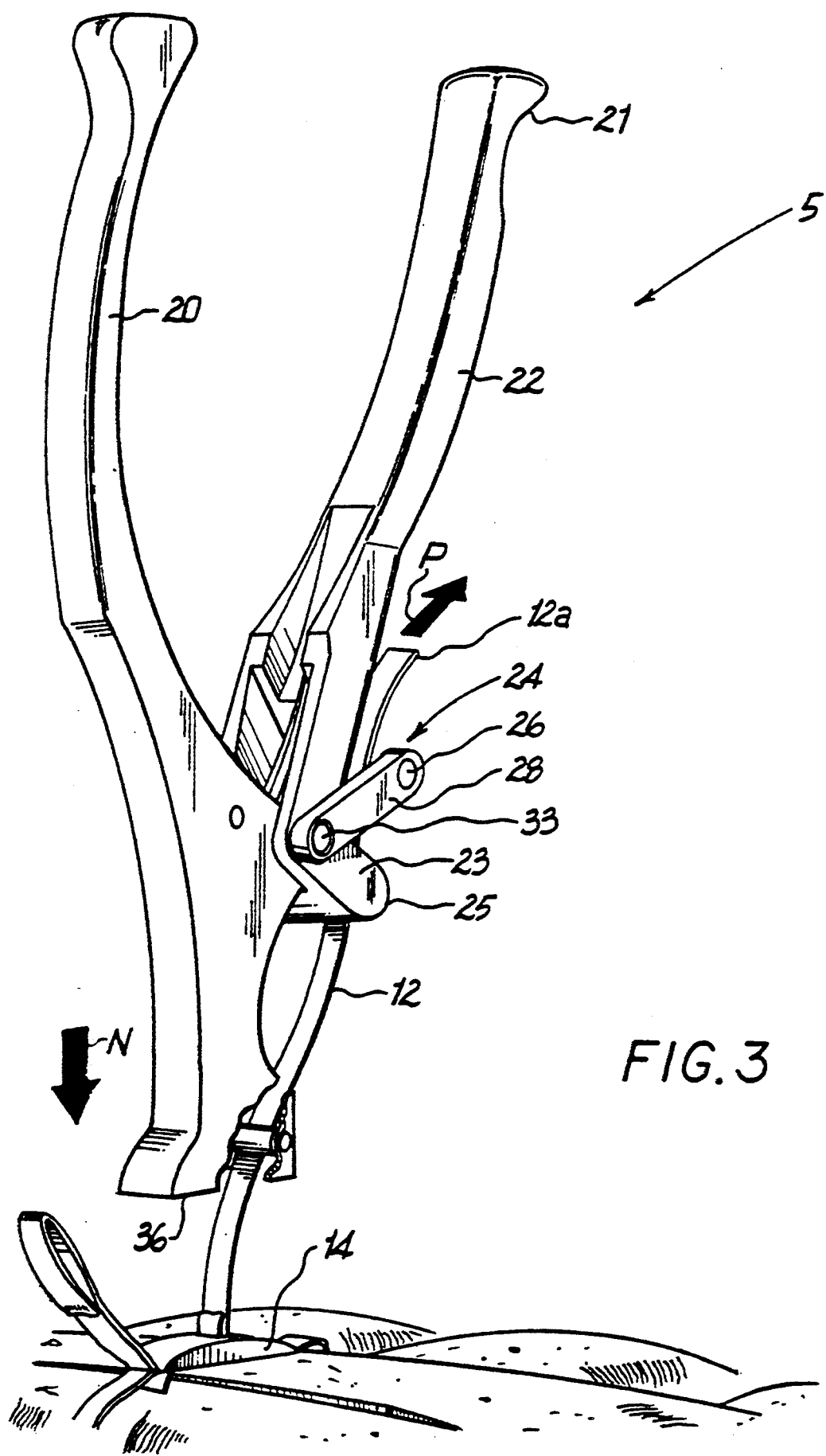
FIG. 3 is a perspective view of the instrument of FIG. 1 showing the wound closure element being inserted into the instrument.

In operation, after the wound closure element is looped around the split portions 11 of sternum 10 and buckle or locking device 14 is positioned against the outer surface of sternum 10, as shown in FIG. 3, the free end of ribbon 12 is routed past roller 34 and inserted between roller 26 of pincher assembly 24 and abutment surface 25 of leg portion 23. Note that pincher assembly 24, which comprises ears 28, 30 and roller 26, is pivoted to its upper position, spaced from abutment surface 25, to create a sufficient gap between roller 26 and abutment surface 25 of leg portion 23 to allow the ribbon 12 to be further rotated in the instrument in the direction of arrow P, as shown in FIG. 3. Once the free end of ribbon 12 is interposed between leg portion 23 and roller 26, pincher assembly 24 is pivoted so that roller 26 returns to the lower position to frictionally retain ribbon 12 between abutment surface 25 and roller 26.

Figure 4A:
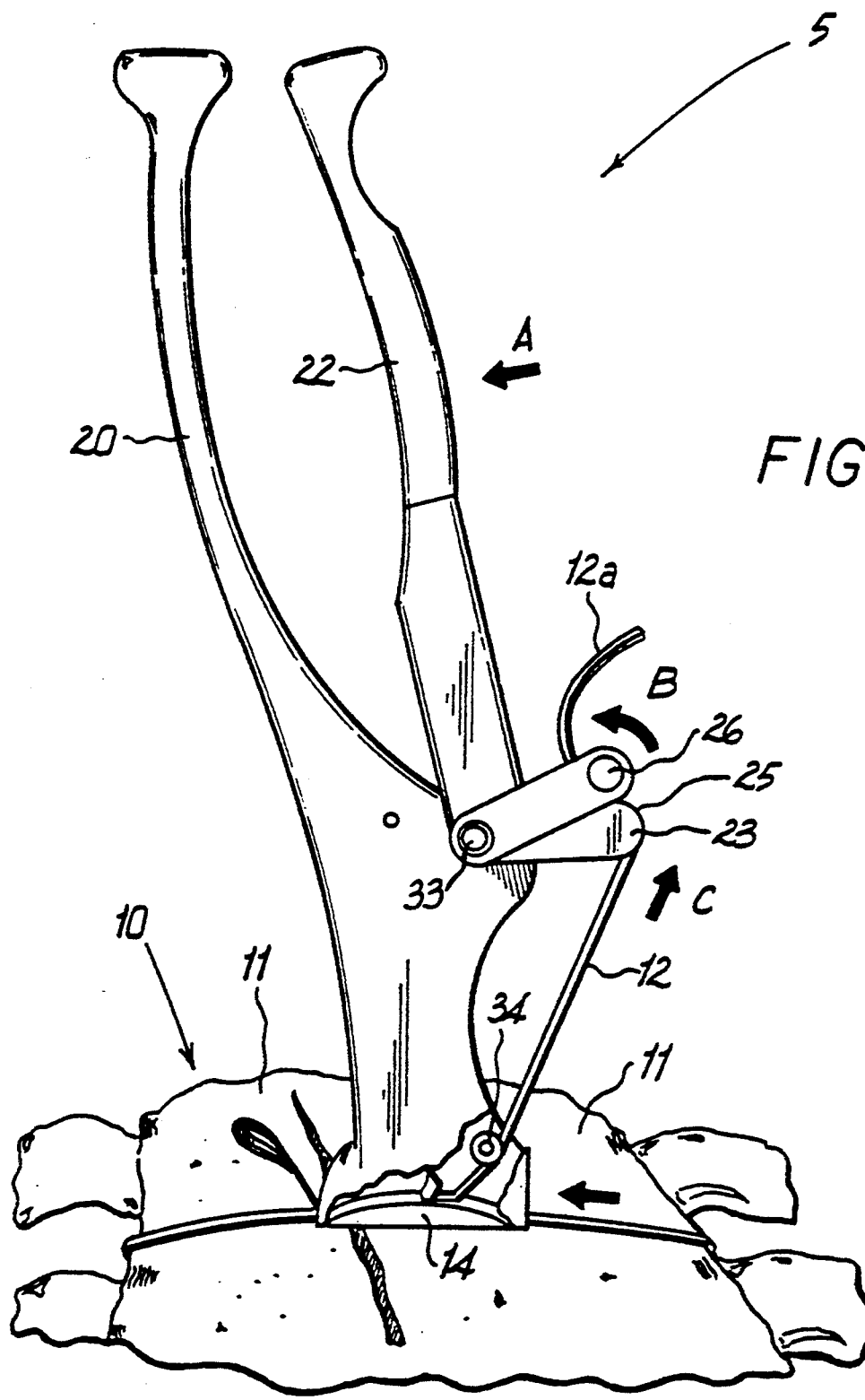
FIG. 4A is a side view of the instrument of FIG. 1 showing closure of the instrument to tighten the wound closure element.
Figure 4B:
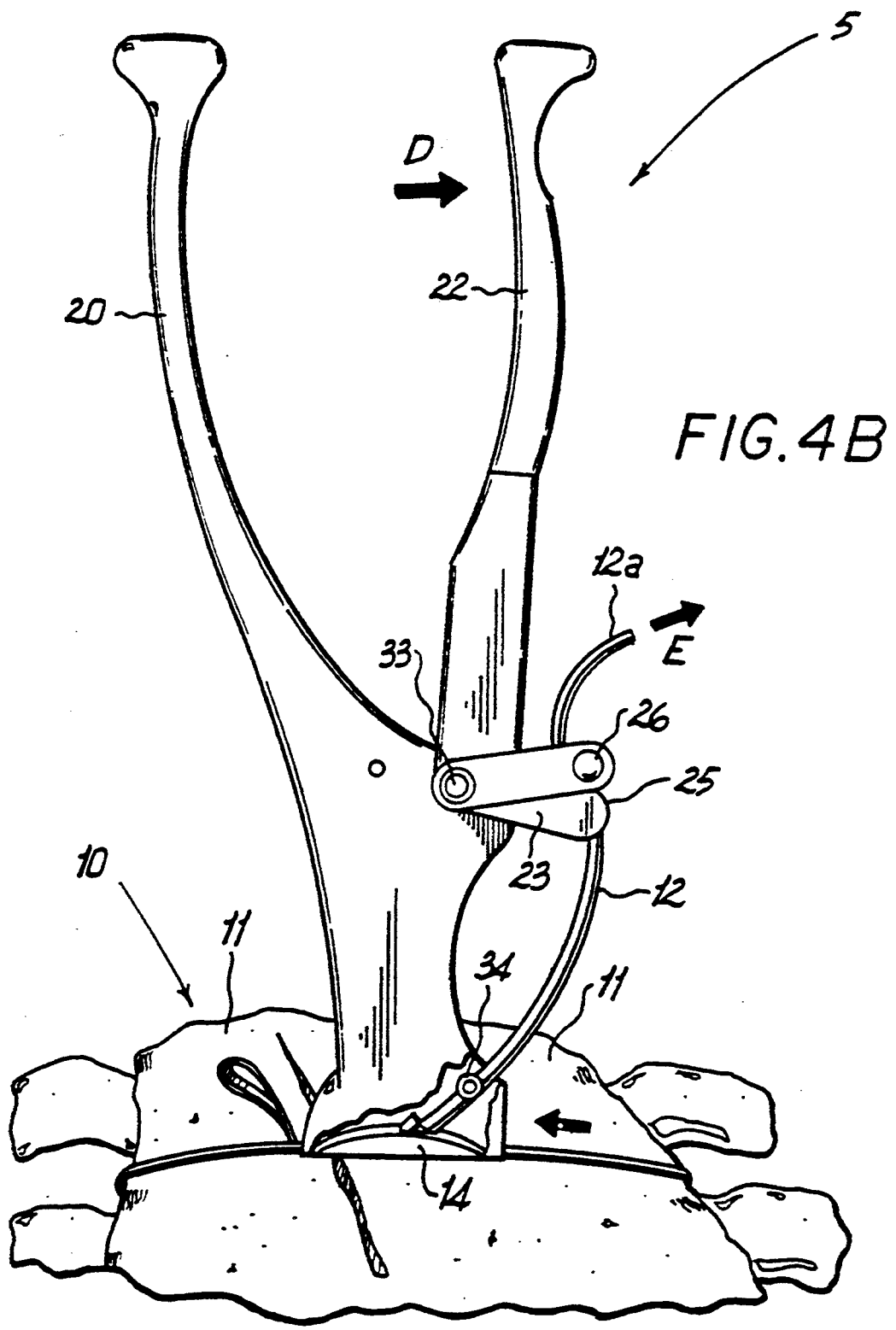
FIG. 4B is a side view showing removal of the slack in the wound closure element after closure of the instrument.

Once ribbon 12 has been routed through instrument 5, the instrument is placed over sternum 10, as shown by arrow N of FIG. 3, so that bottom recess 36 of frame 20 receives and retains buckle 14 therein, as shown in FIG. 4A.

To tighten the wound closure element, handle portion 22 is pivoted inwardly towards frame 20 in the direction of arrow A to the closed position, shown in FIG. 4A. This pivotal movement carries attached leg portion 23 and pincher assembly 24 in an upward direction shown by arrow B. Consequently, ribbon 12 is pulled upwardly in the direction of arrow C through buckle 14, further tightening the wound closure element around the split portions 11 of sternum 10. As previously noted, buckle 14 continuously maintains the tension on ribbon 12 so as to retain ribbon 12 in tight alignment with sternum 10 and facilitate proper healing of the sternum. Handle 20 is then released and returned to its initial open position as shown by arrow D of FIG. 4B. The slack created in the ribbon by its tensioning is then removed by the user manually pulling the free end 12a of ribbon 12, as shown by arrow E in FIG. 4B.

Movement of handle 22 towards frame 20 is then repeated, and the slack manually removed, as described above, the necessary number of times until the desired tension around the sternum is achieved. At this point the excess strap extending from the buckle 14 is cut by a knife or any other suitable means and the bottom portion of frame 20 is disengaged from buckle 14 and the instrument 5 is removed, leaving the sternum split portions tightly closed.

Figure 6:
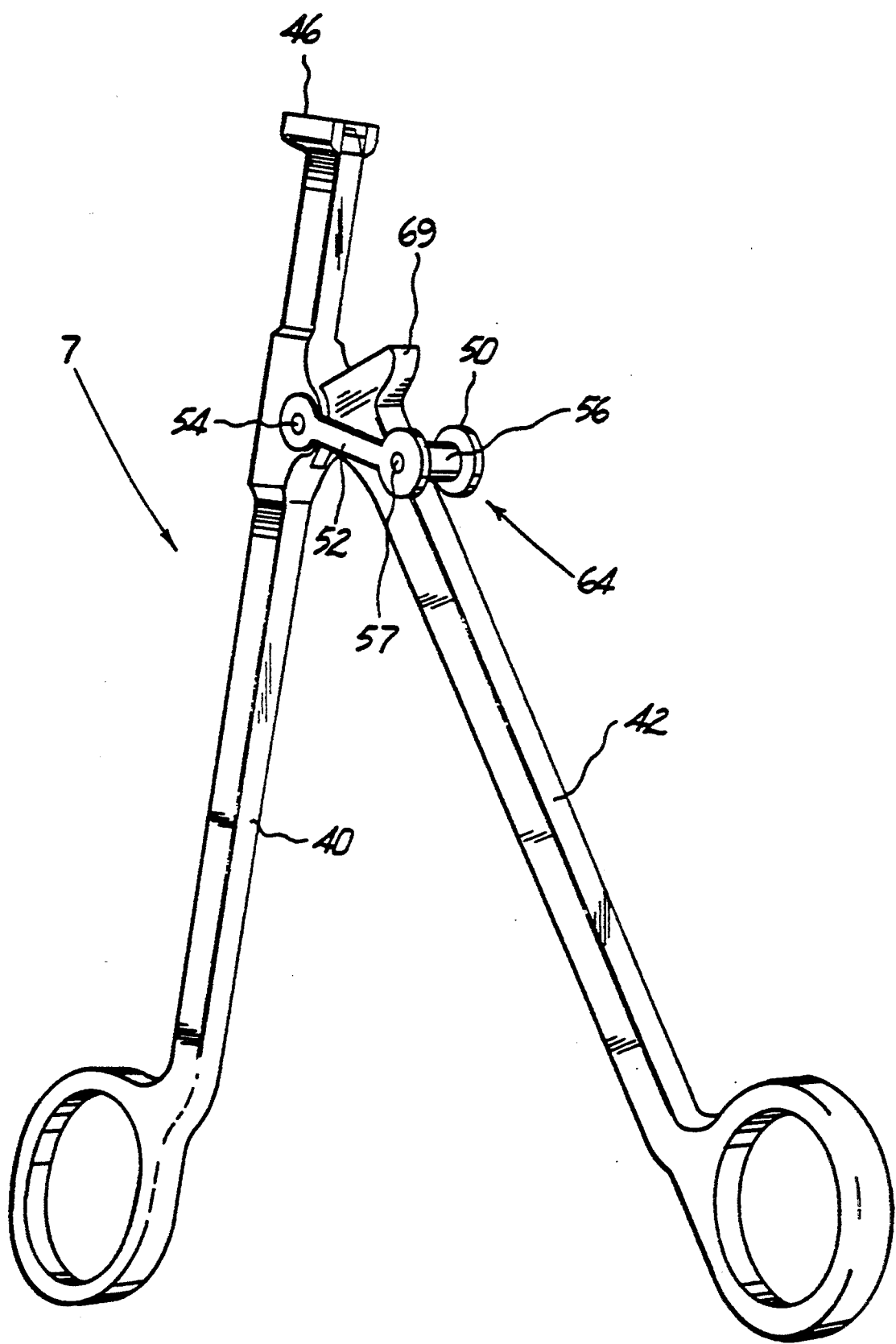
FIG. 6 is a perspective view of an alternative embodiment of an instrument of the present invention for tightening a wound closure element around the sternum.
Figure 7:
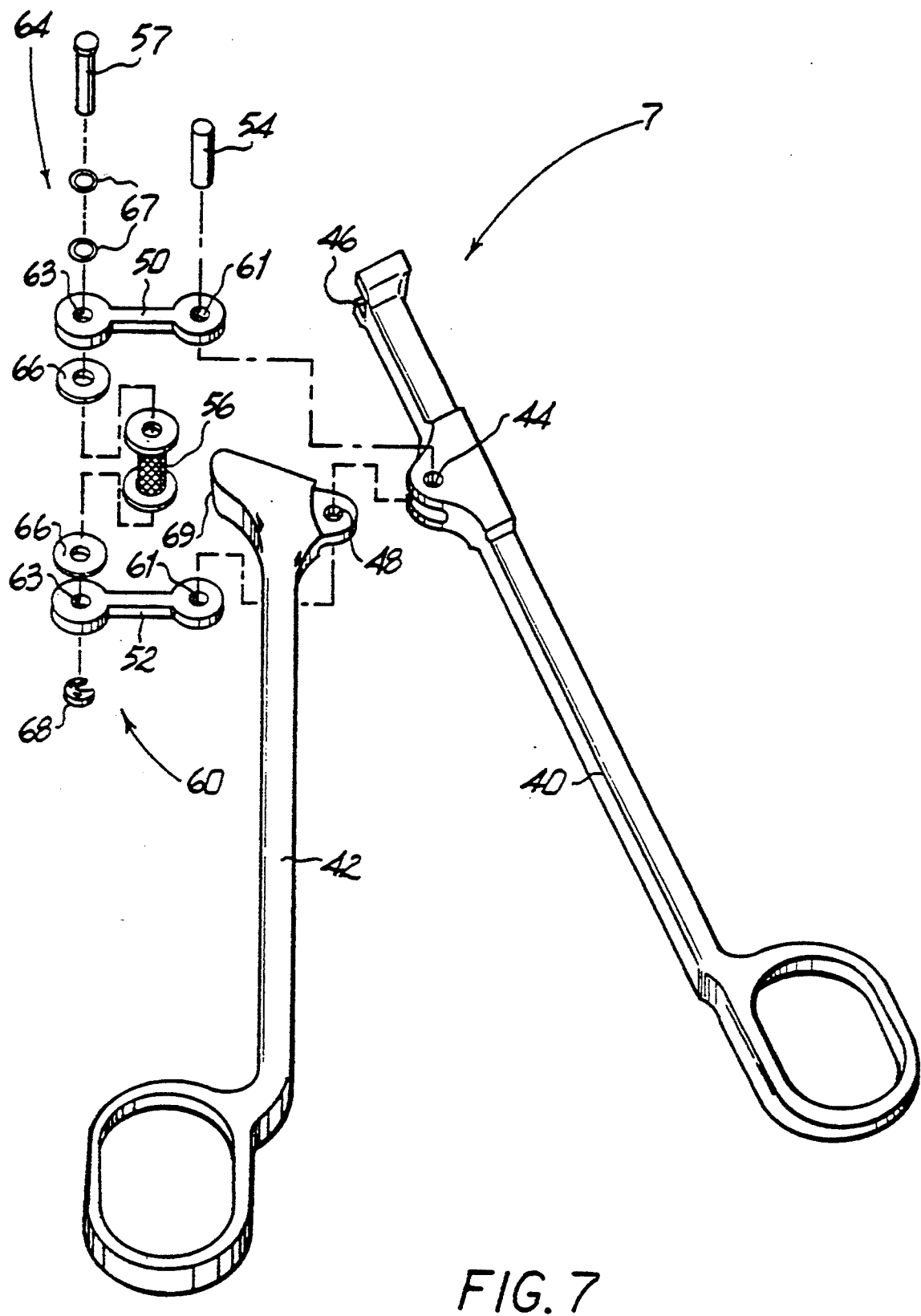
FIG. 7 is an exploded view showing the components of the instrument of FIG. 6.
Figure 8:
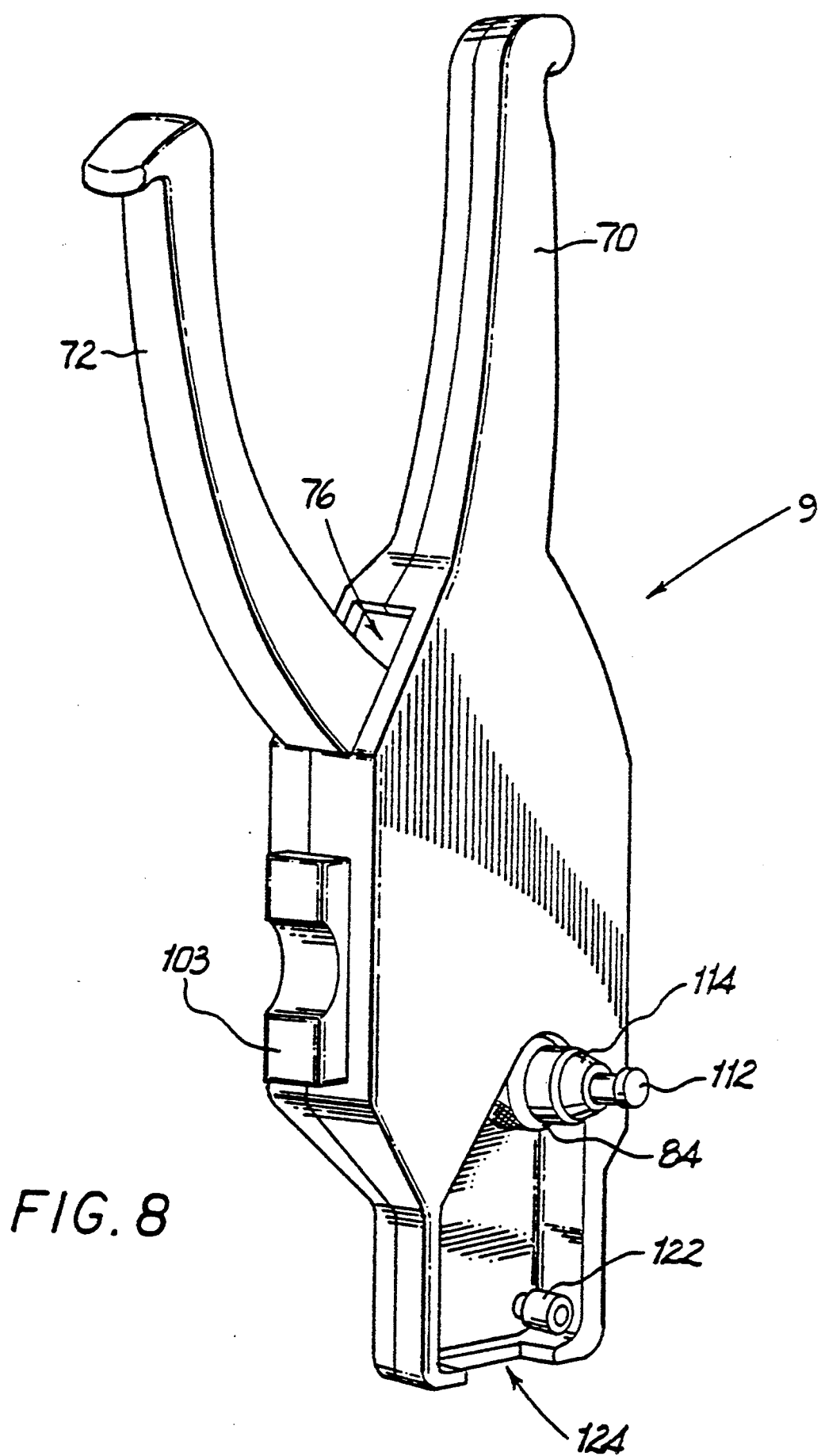
FIG. 8 is a perspective view of another alternative embodiment of an instrument of the present invention for tightening a wound closure element around the sternum.

Referring to FIGS. 6 and 7, an alternative embodiment of the instrument of the present invention utilized for tightening a wound closure element around a body portion such as the sternum is illustrated. The instrument 7 operates in a similar fashion to the instrument 5 of FIGS. 2-5 discussed above, except it is provided with a spring mechanism to provide automatic slippage of the ribbon 12 when a desired tension is reached. This advantageously helps to avoid overtightening and possible breaking of ribbon 12 and avoids damaging the sternum.

Referring to FIG. 7, instrument 7 comprises handle 42 pivotally mounted to frame 40 by mounting rod 54 which extends through aligned openings 44 and 48 in frame 40 and handle 42, respectively. Handle 42 includes a leg portion having an abutment surface 69 for cooperation with pincher mechanism 60. Both frame 40 and handle 42 each terminate in finger loops to facilitate grasping and manipulation of the instrument by the user. The bottom portion of frame 40 includes recess 46 dimensioned to receive buckle 14.

Pincher mechanism 60 is provided to retain and move ribbon 12 in response to pivotal movement of handle 42 and includes left ear 50, right ear 52, knurled roller 56 and clutch mechanism 64. When assembled, opening 61 in left ear 50 and right ear 52 are aligned with openings 44 and 48 in frame 40 and handle 42, respectively. Mounting rod 54 is mounted through openings 61 in the ears 50 and 52 and further through openings 44 and 48 in frame 40 and handle 42 for radial movement of the pincher mechanism 60 thereon. Roller 56 is mounted through openings 63 formed in the outer end portions of ears 50 and 52 in combination with clutch mechanism 64 as will be discussed in more detail below. As in the embodiment of FIG. 2, pincher mechanism 60 pivots between a lower position adjacent abutment surface 69 and an upper position spaced away from abutment surface 69.

The clutch mechanism 64 cooperates with roller 56 and includes clutch pads 66, bellville washers 67, clip 68 and pin 57 all of which are aligned with openings 63 in ears 50 and 52. The clutch mechanism regulates the axial force created by the compression of the bellville washers 67 against roller 56, thereby controlling its resistance to rotation and consequently the tension required to allow slippage of the ribbon. The greater the radial force, the greater the force necessary for roller 56 to slip and consequently the greater the tension which can be applied to ribbon 12.

Turning now to the operation of instrument 7, bellville washers 67 are compressed to a predetermined position corresponding to the desired tension to be exerted on the sternum by ribbon 12. Once bellville washers 67 are compressed, instrument 7 operates in a manner similar to the embodiment of FIGS. 2-5, in that the ribbon (not shown) is routed through the bottom portion of frame 40 and inserted in the gap between roller 56 and abutment surface 69 of handle 42, when pincher assembly is moved upwardly to the upper position. Pivotal movement of pincher assembly 60 to the lower position, frictionally retains ribbon 12 against abutment surface 69. Movement of handle 42 towards frame 40 causes ears 50 and 52 to move upwardly, carrying roller 56 in the same direction. Strap 12, frictionally held between the roller 56 and abutment surface 69, is consequently pulled upwardly to further tighten ribbon 12 around the body portion which it encircles. As mentioned above, buckle 14 continuously maintains the tension on ribbon 12. Handle 42 is then released to return to its open position and the slack in strap 12 is removed by manually pulling the exposed end.

As in the embodiment of FIGS. 2-5, the steps of squeezing (closing) and releasing (opening) the handle are repeated until the sternum obtains the desired degree of closure, i.e. the maximum desired tensioning force is applied by the ribbon against the sternum. At this point, further attempts to tighten ribbon 12 by pivoting handle 42 inwardly towards frame 40 will cause roller 56 to slip rather than maintain its grip on the ribbon. Consequently, the ribbon will not be pulled upwardly and hence the ribbon will not be tightened. As noted above, excess ribbon may be cut by any suitable means and instrument 7 may then be removed from the wound closure element.

Referring now to FIGS. 8-11, another alternative embodiment of the instrument for tightening an elongated wound closure element is illustrated. In this embodiment, movement of the handle 72 with respect to the frame 70 actuates a rotatable gripping roller which operates to pull the ribbon tighter against the body portion. Manual pulling of the ribbon by the user is eliminated.

Figure 9:
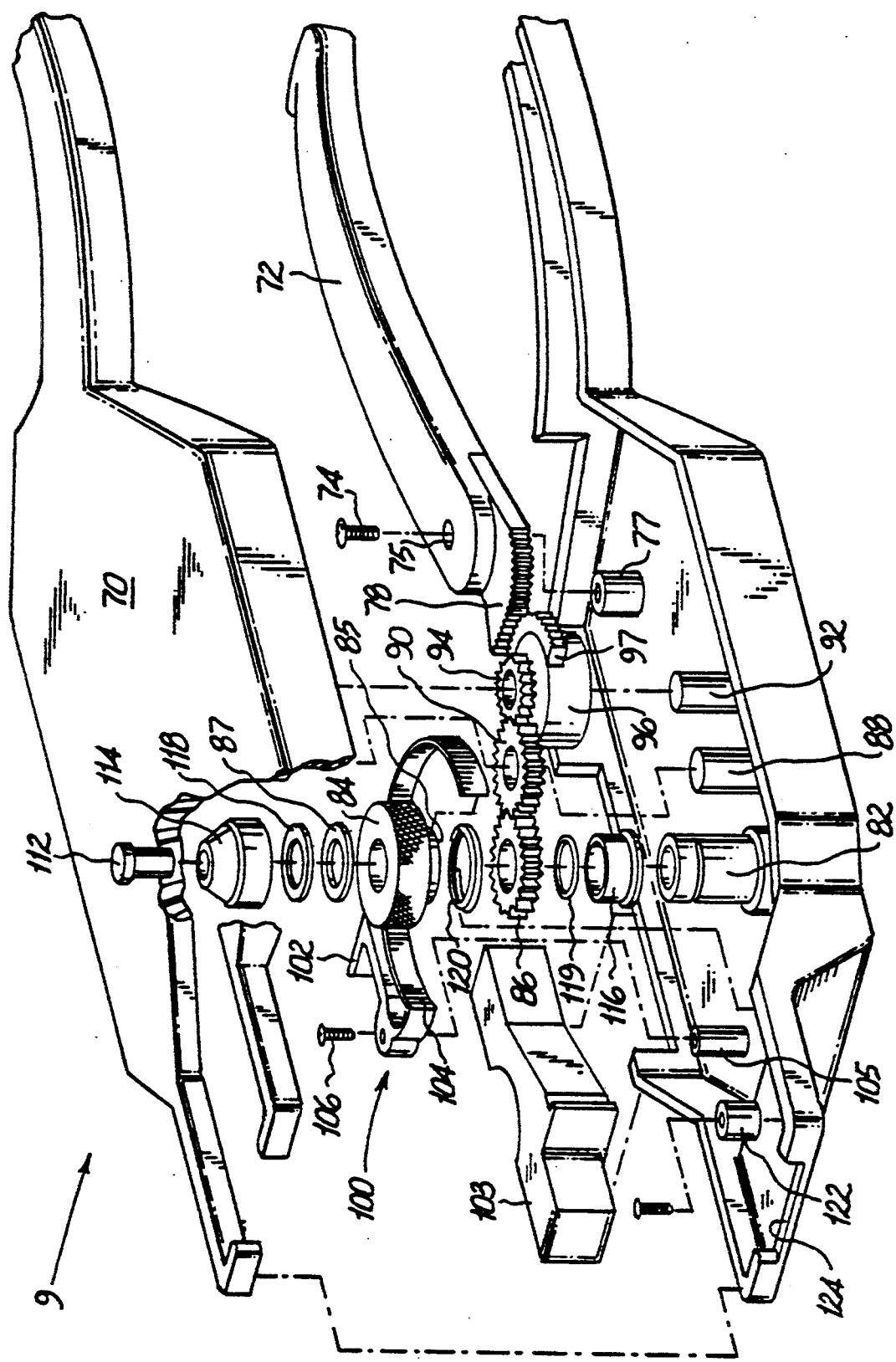
FIG. 9 is an exploded view showing the components of the instrument of FIG. 8.
Figure 10:
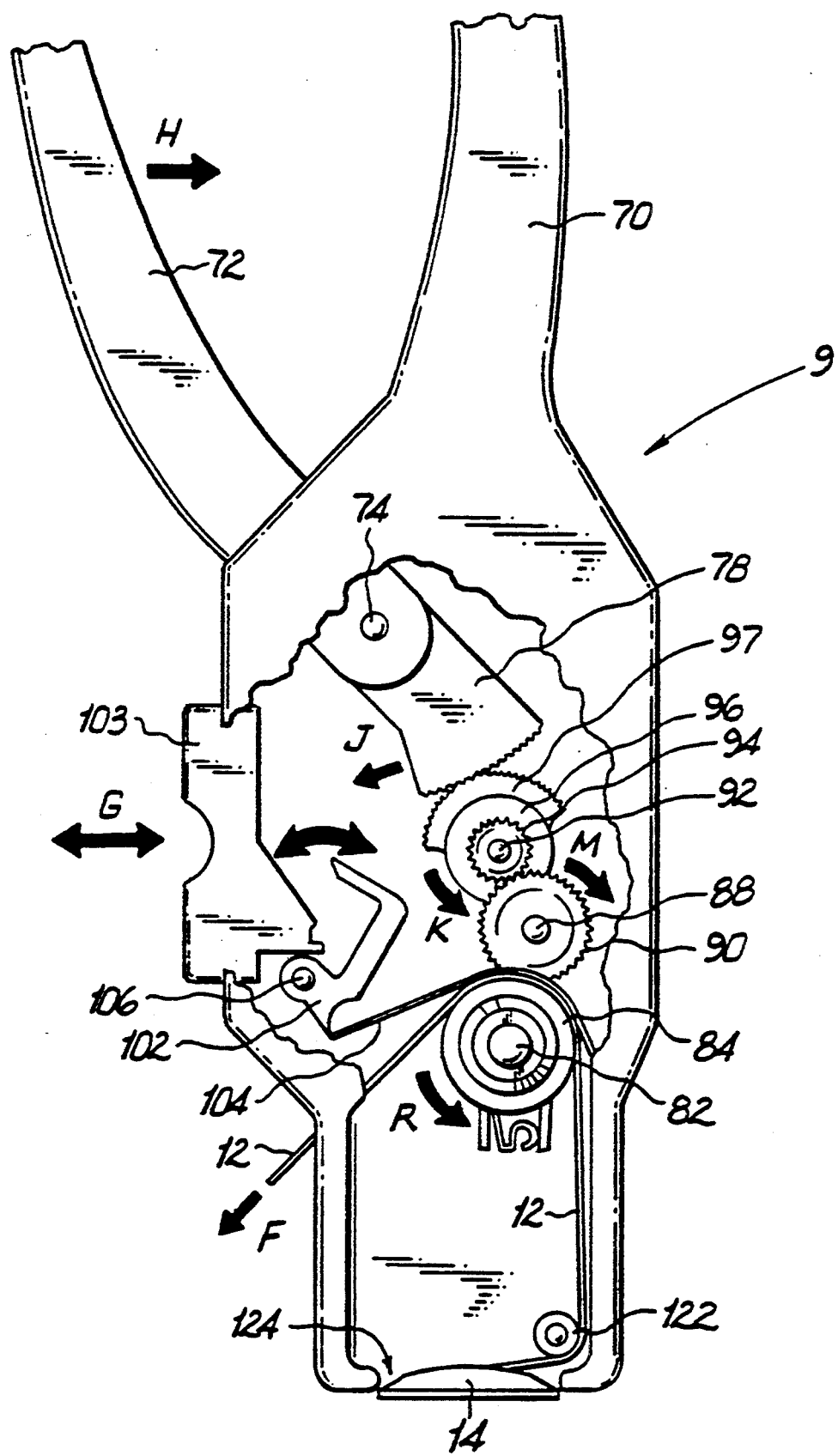
FIG. 10 is a side view of the instrument of FIG. 8 with a portion of the housing cut away to show movement of the components during closure of the instrument handle.
Figure 11:
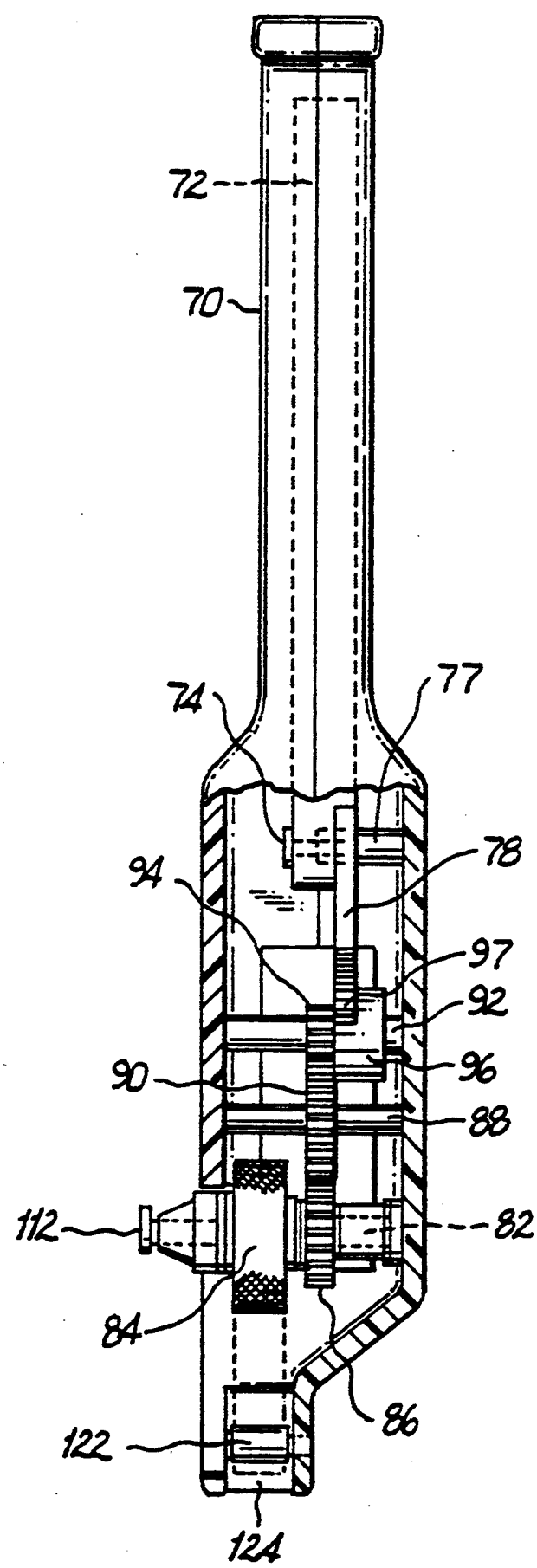
FIG. 11 is a longitudinal cross-sectional view of the instrument of FIG. 8.

With particular reference to FIGS. 9-11, instrument 9 has a frame 70, pivotable handle 72 mounted thereto and a ribbon driving mechanism which functions to pull the ribbon in the direction of arrow F, shown in FIG. 10, in response to pivotal movement of handle 72. Frame 70 also includes an actuating mechanism which cooperates with handle 72 to actuate the ribbon tightening mechanism and a clamping mechanism for retaining the ribbon against the driving mechanism during operation of the instrument.

Referring to FIG. 9, handle 72 is mounted to frame 70 via pin 74 extending into cylindrical holder 77, as shown. Handle 72 has a proximal lever portion 78 which initiates movement of the actuating mechanism in response to pivotal movement of handle 72 to its closed position in a direction towards frame 70. Frame 70 includes bottom recess 124 adapted to receive buckle 14 of the wound closure element. Bottom roller 122, positioned adjacent to recess 124, engages a portion of ribbon 12 to restrict its movement in the instrument during tightening.

The ribbon driving mechanism includes roller 84 which is rotatably mounted on a central shaft 82, and supported by beatings 114 and 116. Preferably, roller 84 is knurled to improve fictional engagement with ribbon 12. The driving mechanism further includes a tension control mechanism to provide for slippage of roller 84 when the maximum tension around the sternum is achieved in order to prevent overtightening of ribbon 12 and possible snapping or tearing of the ribbon, or damaging the sternum.

More specifically, the tension control mechanism is mounted on central shaft 82 between the bearings of the ribbon driving mechanism. The tension control mechanism includes wrap spring clutch 120, bellville washers 118 and 119 and an adjusting screw 112. Wrap spring clutch 120 is mounted on the hub 85 of roller 84 adjacent to lower gear/clutch plate 86 and is provided to prevent reverse rotation of shaft 82, and hence prevents slacking of the ribbon. Clutch plate 87 is positioned about central shaft 82 between bellville washer 118 and roller 84, and adjusting screw 112 is inserted through openings in beatings 114 and 116 and through spring clutch 120 into an axial opening formed in central shaft 82. The degree of tightening of screw 112 will effect the ease of rotation of roller 84 which can therefore set to extent of tightening of ribbon 12.

The drive mechanism for actuating the ribbon tightening mechanism comprises lower gear/clutch plate 86, middle gear 90 and small gear 94 mounted to upper wheel or roller clutch 96. Lower gear 86 is mounted on central shaft 82 and meshes with the teeth of middle gear 90 to axially rotate shaft 82 in response to rotation of middle gear 90. Middle gear 90 is rotatably mounted on lower shaft 88 which is connected to an inside portion of frame 70. Middle gear 90 is interposed between lower gear 86 and small gear 94 so that rotation of small gear 94 will cause rotation of lower gear 86 in the same direction at small gear 94. Small gear 94 is positioned adjacent to roller clutch 96 and fixedly secured to rotatable shaft 92 so that the fixed point of small gear 94 allows it to rotate in only one direction when roller clutch 96 is rotated. Roller clutch 96 includes a one-way clutch secured to shaft 92 to limit rotation of small gear 94 to a single direction and an arcuate portion 97 which engages lever portion 78 of handle 72. Consequently, pivotal rotation of handle 72 actuates roller clutch 96 and will be discussed in more detail below.

Turning now to the clamping mechanism 100 and with continued reference to FIG. 9, the clamping mechanism includes a clamping lever 102 movable about pivot pin 106 between a disengaged position spaced from roller 84 and an engaged position wherein material engaging surface 104 of clamping lever 102 presses the ribbon against roller 84 to help retain it in position during operation of the instrument. As shown, pivot pin 106 is inserted through an opening in clamping lever 102, extends into cylindrical retainer 105 and is mounted to the inner portion of the frame 70 to secure lever 102 to frame 70. Actuation knob 103 protrudes through an outer surface of the instrument, as shown in FIG. 10, providing the user with easy access thereto. Knob 103 is movable between inner and outer positions as shown by arrow G in FIG. 10, to move engaging surface 104 of lever 102 between its engaged and disengaged positions.

Turning now to the operation of instrument 9, and more particularly to FIG. 10, one end of ribbon 12 is routed through bottom recess 124 of frame 70, around bottom roller 122 and roller 84. The instrument 9 is then placed over buckle 14, shown in FIG. 9, in a similar manner, as described in the embodiments of FIGS. 2 and 6. Latch 103 is pressed inwardly to bias engaging surface lever 102 against ribbon 12 to help retain it against roller 84 and readjust the instrument for use.

To tighten the ribbon around the body portion, e.g. the sternum, handle 72 is pivoted inwardly, in the direction of arrow H, towards frame 70 to its closed position, causing lever 78 to move in the direction of arrow J, as shown in FIG. 10. This results in counterclockwise rotation, shown by arrow K, of roller clutch 96 through the one-way clutch (secured within roller clutch 96, as noted above), driving shaft 92 and fixed small gear 94. Counterclockwise rotation of small gear 94 causes rotation of middle gear 90 in the opposite direction, shown by arrow M, consequently causing counterclockwise rotation of meshed lower gear 86, as shown by arrow R. Rotation of lower gear 86 rotates central shaft 82, causing roller 84 to be frictionally driven by clutch plate 87 and lower gear/clutch plate 86 mounted on shaft 82 adjacent to roller 84 to rotate in the same counterclockwise direction. As roller 84 rotates, it pulls ribbon 12 in the direction of arrow F. The knurled surface of the roller 84 helps to prevent slippage of ribbon 12 which might otherwise occur if the roller 84 had a smooth surface. Bottom roller 122 facilitates upward sliding of ribbon 12 and further restrains ribbon 12 from moving transversely within the instrument.

Return of handle 72 to its normal outer position, causes upper gear 96 by way of the one-way clutch of roller clutch 96 secured to shaft 92 to rotate clockwise to return to its original position. During this return stroke, small gear 94 remains stationary due to its fixed point which permits rotation in only one direction and therefore middle gear 90, lower gear 86, and roller 84 also remain in their position due to wrap spring clutch 120 engaging onto hub of roller 84 thereby maintaining strap 12 in its tighter position. Repetition of the above steps (i.e., squeezing of handle 72 towards frame 70 and release of handle 72) is continued until the strap is tightened to the desired level. Note that the desired degree of tightening is set prior to operation of the instrument by adjustment of screw 112 adjusting the compressive force of bellville washers 118 and 119. Thus, sufficient tensioning is automatically accounted for and overtightening of the strap is prevented when the predetermined tension is achieved. Further squeezing of handle 72 will prevent roller 84 from rotating, due to clutch plate 87 and lower gear/clutch plate 86 that is driven by shaft 82, which slip on the frictional surfaces of roller 84 thereby preventing overtightening and possible strap breakage.

It will be understood that the foregoing is illustrative of the principals of the invention and that various modifications can be made by those skilled in the art without departing from the scope and spirit of the present invention.

What is claimed is:

1. An apparatus for tightening an elongated wound closure element about tissue, which comprises:
   frame means;
   handle means pivotally mounted about a pivot pin to said frame means; and a pincher assembly pivotally mounted to said frame means about said pivot pin and pivotally movable relative to said handle means between an open and a closed position, said pincher assembly adapted for securely wedging one end portion of a wound closure element against a bearing surface defined by said handle means when in said closed position and permitting passage of the one end portion of the wound closure element between said pincher assembly and said bearing surface when in said open position.

2. The apparatus according to claim 1 wherein said pincher assembly comprises at least one linkage member pivotally mounted at a first end portion thereof to said pivot pin and an engaging member mounted to said linkage member at a second end portion thereof, said engaging member engaging the one end portion of the wound closure element when said pincher assembly is in said closed position.

3. The apparatus according to claim 2 wherein said engaging member includes a knurled surface to facilitate engagement of the wound closure element.

4. The apparatus according to claim 3 wherein said engaging member is cylindrical in shape.

5. The apparatus according to claim 3 wherein said pincher assembly comprises two of said linkage members, said linkage members positioned and adapted to support said engaging member.

6. The apparatus according to claim 5 wherein the one end portion of the wound closure element is passed through an opening defined between said engaging member, said bearing surface of said frame means and said linkage members when said pincher assembly is in said open position.

7. The apparatus according to claim 6 wherein said engaging member is securely fixed to said linkage members.

8. The apparatus according to claim 1 wherein said pincher assembly comprises clutch means for preventing further tensioning of the wound closure element when the tension in the wound closure element exceeds a predetermined value.

9. The apparatus according to claim 8 further comprising means for controlling the level of tension required to release said clutch means.

10. An apparatus for tissue repair, which comprises:
a wound closure material adapted to be looped about split portions of tissue and having first and second end portions, said wound closure material having a locking device attached to said first end portion thereof;
frame means including support means for supporting said locking device attached to said first end portion of said wound closure material, said support means including an opening formed in a lower surface of said frame means, said opening dimensioned and configured to receive and support said locking device;
handle means pivotally mounted about a pivot pin to said frame means; and
retaining means positioned adjacent said handle means for retaining said second end portion of said wound closure material in a generally fixed position relative to said handle means wherein pivotal movement of said handle means in a first direction advances said wound closure material in a tensioning direction about the tissue.

11. The apparatus according to claim 10 wherein said frame means includes a channel in communication with said opening and dimensioned to receive said second end portion of said wound closure material therethrough upon tensioning of said wound closure material.

12. The apparatus according to claim 11 further comprising roller means rotatably mounted within said channel of said frame means for facilitating passage of said second end portion of said wound closure material through said channel upon tensioning of said wound closure material about the tissue.

13. An apparatus for tightening an elongated wound closure element about tissue, the wound closure element having a buckle member attached to a first end portion thereof and a free second end portion, the apparatus comprising:
a frame member including an opening disposed in a lower surface portion thereof for reception and support of the buckle member and a channel in alignment with said opening, said channel dimensioned for reception of the free end portion of the wound closure element to permit passage thereof upon tensioning of the closure element about the tissue;
a handle member pivotally mounted about a pivot pin to said frame member and defining a closure element bearing surface; and
a retaining member mounted to said frame member and movable between a first position wherein said retaining member securely wedges the closure element against said bearing surface of said handle member and a second position wherein said retaining member is displaced from said closure element bearing surface to permit passage of the free end portion of the closure element through said frame member;
whereby pivotal movement of said handle member in a first direction advances the closure element in a tensioning direction about the tissue when said retaining member is in said first position.

14. The apparatus according to claim 13 wherein said retaining member is supported by at least one linkage member, said at least one linkage member pivotally mounted to said frame member and adapted to pivot to move said retaining member between said first and second positions.

15. The apparatus according to claim 14 comprising two of said linkage members, said two linkage members positioned and adapted to support said retaining member therebetween.

16. The apparatus according to claim 15 wherein said retaining member is a cylindrical member.

17. The apparatus according to claim 16 wherein said retaining member includes a knurled surface to facilitate engagement with the free end of the closure element.

18. The apparatus according to claim 15 wherein said cylindrical member is securely attached to said linkage members.

19. The apparatus according to claim 15 further comprising clutch means for preventing further tensioning of the wound closure element when the tension in the wound closure element exceeds a predetermined value.

20. The apparatus according to claim 19 wherein said clutch means comprises clutch pads disposed between respective first and second end surfaces of said cylindrical member and said first and second linkage members.

* * * * *